United States Patent [19]

Pitts

[11] Patent Number: 5,023,819

[45] Date of Patent: Jun. 11, 1991

[54] LINEAR SHAPED FILTER

[75] Inventor: Alan J. Pitts, Comanche, Okla.

[73] Assignee: Halliburton Company, Duncan, Okla.

[21] Appl. No.: 360,510

[22] Filed: Jun. 2, 1989

[51] Int. Cl.$^5$ .......................... G01N 7/00; G06G 7/12
[52] U.S. Cl. ................................. 364/558; 364/581;
   364/572; 250/260; 250/363.01; 73/151
[58] Field of Search .................. 364/558, 550, 551.01,
   364/555, 554, 572, 581, 724.01, 724.08, 724.17,
   724.19, 724.20; 377/10, 15, 19, 20, 1; 166/247,
   250, 253, 286, 292, 295, 64, 66, 92; 250/256,
   259, 260, 253, 482.1, 362, 363.01, 363.03, 366,
   369; 73/151, 152, 445, 450

[56] References Cited

U.S. PATENT DOCUMENTS

| | | | |
|---|---|---|---|
| 3,657,532 | 4/1972 | Zimmerman | 250/435 D |
| 4,395,762 | 7/1983 | Wondergem et al. | 364/554 X |
| 4,403,298 | 9/1983 | May, Jr. | 364/724.19 |
| 4,491,701 | 1/1985 | Duttweiler et al. | 364/724.19 |
| 4,494,214 | 1/1985 | Bernard et al. | 364/724.19 |
| 4,554,633 | 11/1985 | Glover et al. | 364/572 X |
| 4,561,065 | 12/1985 | Matsuda | 364/724.17 |
| 4,575,810 | 3/1986 | Stoub | 364/581 |
| 4,590,579 | 5/1986 | Erb | 364/558 |
| 4,618,939 | 10/1986 | Davis | 364/555 |
| 4,654,802 | 3/1987 | Davis | 364/558 X |
| 4,665,486 | 5/1987 | Shultz | 364/572 X |
| 4,792,915 | 12/1988 | Adams | 364/724.19 |
| 4,837,705 | 6/1989 | Mussler et al. | 364/484 |

Primary Examiner—Joseph L. Dixon
Attorney, Agent, or Firm—James R. Duzan; Mark E. McBurney

[57] ABSTRACT

A filter for use with a signal which varies about a mean, such as in a radioactive densometer, is provided and includes a microprocessor and timing clock for sampling the random variable over a specific time interval. The microprocessor utilizes a weighting factor which is used to determine a percentage of an average frequency of an initial sample of random signals or mean. Further, the microprocessor determines a percentage of an average frequency of a subsequent sample of random signals. Once determined, the two percentages are added together yielding a new frequency which the microprocessor then uses to decide if an actual change in state has occurred.

13 Claims, 3 Drawing Sheets

LINEAR SHAPED FILTER

BACKGROUND OF THE INVENTION

A major portion of the services provided by the oil field service industry relate to cementing operations, including primary cementing, that is, cementing casing into a well bore by pumping cement slurry down a centralized casing and up into the annulus between the well bore and the casing, and squeeze cementing of a particular zone or interval. Additionally, cement slurry is often pumped downhole for water control, fluid loss control, and many other purposes.

Another aspect of the oil field service industry is stimulation services which include, among other operations, fracturing an oil bearing formation by pumping a pressurized fluid into well bore perforations until the oil bearing formation fractures. A proppant laden slurry is then pumped down hole after the fracturing fluid. This fracture is then held open by the proppant, usually sand or bauxite, which remains embedded in the walls of the fracture after the fluid contained within the slurry migrates into the surrounding formation, or, ideally, is flowed back into the well bore out of the formation when pressure is reduced.

In all of the aforementioned situations it would be advantageous to have a quick-response system for determining the density of the cement slurry, or the proppant slurry.

In oil well cementing operations, the density of the cementing slurry is an important factor. The bore hole cementing fluid typically is a slurry of chemical constituents mixed with water and has a certain density. Should the composition of the slurry mixture change during the pumping operation, the density changes and a change in mixture can effect desired results in the cementing operation. For that reason, it is desirable to be able to sense changes in density, i.e. changes in the mixture in order to be able to provide a correction to the mixture before a large volume of incorrect mixture is introduced into the system.

Similarly, in fracturing of wells, monitoring of the density of the fracturing fluid, or proppant slurry, is desirable to ensure that there is not too little proppant in the slurry, which can result in fracture closure, or too much proppant, which can result in "sand out", or termination of the operation due to plugging of the pump, lines or well bore with proppant.

It is accordingly, a feature of the present invention to obtain a relatively quick-response time to the change of density in a cementing or fracturing fluid system so that the fluid may be continuously monitored and corrected if necessary to obtain a consistent density for the fluid mixture.

The present invention relates to a method and apparatus for processing randomly varying data to obtain quick response control to changes in the density of a fluid.

The prior art has developed digitally processed data for nuclear densometers, as illustrated by U.S. Pat. No. 3,657,532, issued to Carl W. Zimmerman. As set forth in the '532 patent, digital systems allow the incorporation of reliable, inexpensive and compact integrated circuits and can be used to develop digital pulse counting techniques. However, in this prior art apparatus, there remains a substantially long time response to a change in density in the fluid sample being tested, and as a consequence, a considerable volume of incorrect density fluid may be passed through the system for use before a correction in the density can be detected or made.

U.S. Pat. No. 4,618,939 to Davis and assigned to the assignee of the present invention involves a method and system for sensing the density of a fluid and for providing statistical count signals which are proportional to density. This prior art system only identifies significant changes in density and then responds to these changes only after a substantial period of time.

Additionally, U.S. patent application Ser. No. 262,406, filed Oct. 25, 1988 and assigned to the assignee of the present invention describes a digital filter which can be used with a radioactive densometer. The digital filter uses a weighting factor including two confidence factors to determine whether or not an actual change in state has occurred.

SUMMARY OF THE INVENTION

A filter for use in a central processing unit (CPU) is provided which can quickly detect actual changes in the state of data which varies randomly about a mean. For example, a radioactive source provides emissions which vary randomly about a mean, some of which are absorbed by the fluid to be measured. The remaining emissions being counts which are a function of the density of the fluid. The present invention provides an accurate and quick means of determining whether a change in state (such as density) has actually occurred. The CPU is programmed such that the difference between the average frequency of the counts ($f_o$), i.e. the mean, and the frequency of the next successive sample of counts ($f_1$), divided by the number of standard deviations therebetween and a dampening factor, update a weighting factor accordingly. Thus, the further a count is from the mean, the more quickly the density reading is changed.

Therefore, in accordance with the previous summary, objects, features and advantages of the present invention will become apparent to one skilled in the art from the subsequent description and the appended claims taken in conjunction with the accompanying drawings.

DETAILED DESCRIPTION OF THE PREFERRED EMBODIMENTS

Figure 1:
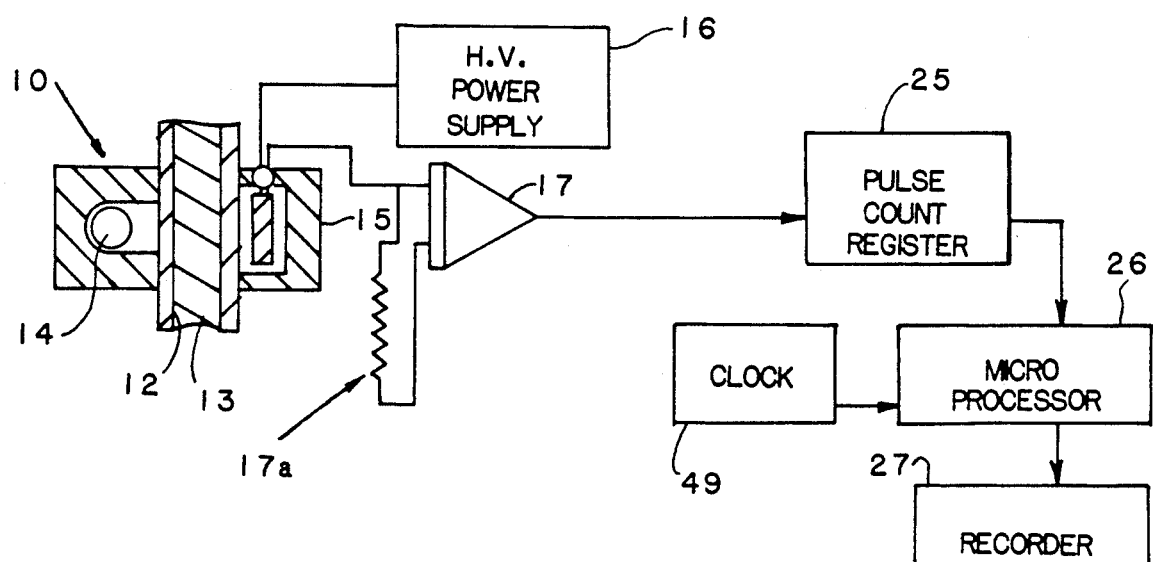
FIG. 1 is a schematic block diagram depicting a radioactive densometer system which can utilize the present invention.

Referring now to FIG. 1, use of the invention in the context of cementing a well bore is described. A housing 10 is mounted on a tubular pipe with a bore 12 through which a well cementing fluid 13 is caused to flow between cementing tanks or trucks (not shown) and a well bore to be cemented (not shown). A source of radiation 14 is located on one side of a tubular pipe including bore 12 and, on an opposite side, a radiation detector 15 is located. The radiation provided by the source 14 is a constant intensity over a substantial period of time (randomly varying about a mean over a short period of time) of gamma ray emissions. A substantial period of time being a time period much less than the half life of the source of radiation. The gamma rays are transmitted through the material surrounding the bore 12, the slurry of cement 13 within the bore and to the detector 15. The detector 15 may be, for example, a crystal of sodium or cesium iodide (thallium activated) or other material capable of scintillating under irradiation and may include an electron photo multiplier tube for converting light flashes of the scintillation of the crystal into an electrical pulse. It can readily be seen that the only variable with respect to density between the source 14 and detector 15 is the cement slurry 13. A percentage of the gamma rays emitted by the source 14 are absorbed or attenuated by the cement slurry 13 and do not reach the detector 15. Thus the counting rate of the output signal from the photo multiplier tube of the detector 15 is similarly related to the density of cement slurry 13 through which the rays must pass to reach the crystal in the detector 15 and the intensity of the source 14.

The detector 15 is powered by a high voltage power supply 16 and the output signals from the detector 15 are supplied to a comparator circuit 17. The comparator circuit 17 eliminates extraneous noise signals below a selected amplitude level determined by a reference level set by resistor 17A, and amplifies the output signals which are passed through the circuit. The output of the comparator circuit 17 represents count pulses above the threshold level set by the resistor 17A.

The output signals from the comparator 17 are applied to a counter register 25 and the counter register 25 outputs to a computer 26. The computer may be a OKI Semiconductor 8085 microprocessor or other suitable CPU. The microprocessor 26 is keyed by a clock 49 to systematically and regularly process the counts in the register 25. The computer 26, upon processing of the data, may provide an output to an optional recorder 27.

Figure 3:
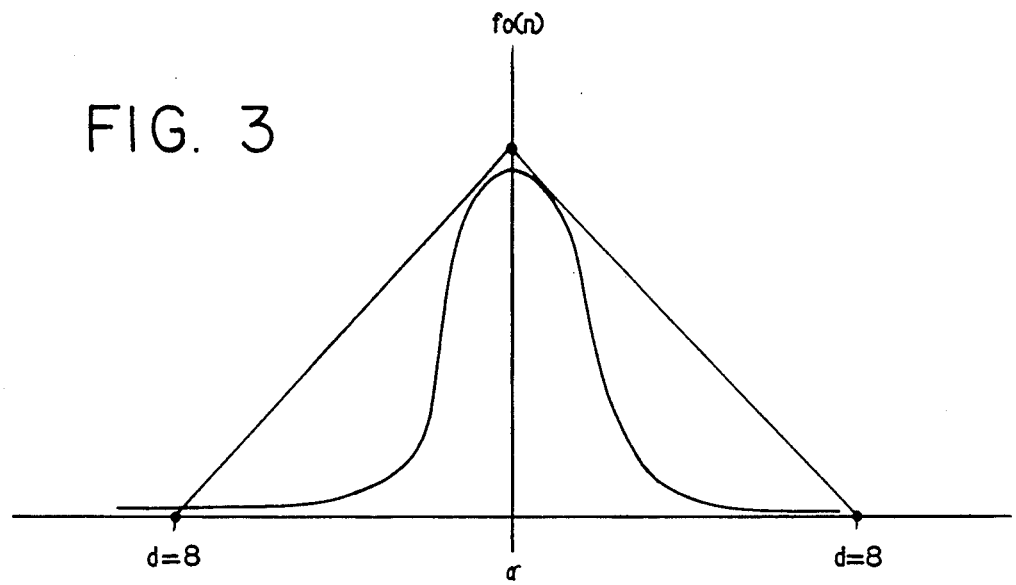
FIG. 3 is a graph representing the poisson distribution function of the counts under steady state conditions and the linear approximation which is dependent upon the value of the dampening factor.

The filter determines a "best estimate" for mean frequency which is based on information currently available. Initially, since no information is available, the mean frequency is arbitrarily assumed to be one (1). As information becomes available, due to a sampling of counts being taken, an estimate for the mean frequency can be made, i.e. $f_{o(n)}$ for any time n. Further, successive estimates can be made $f_{o(n+1)}$ *for each successive time period during which counts are sampled. This estimated mean frequency is shown as* $f_o$ on FIG. 3, whereas the horizontal axis of FIG. 3 represents the number of standard deviations from the mean of the counts. The vertical axis of FIG. 3 represents the probability of occurrence. In other words, FIG. 3 is an illustration of a poisson distribution which closely approximates the normal distribution function.

The filter of the present invention uses a weighting factor which reflects the confidence which is based on the probability of statistical deviations relative to the mean. For example, the greater the distance (number of standard deviations) between the mean and the sampled data, the greater the confidence. Stated another way, the more standard deviations away from the mean value, the greater the mean, as shown on FIG. 3, is changed each time action is taken. The greater the confidence (and thus the greater the weighting factor) the more drastic is the action to be taken. For example, if a data sample is received three or more standard deviations from the mean, then the confidence is high. Thus, fairly drastic action would be taken to change the mean to correspond to the newly received data.

However, if the new data were less than one standard deviations from the mean, then small action would be taken (i.e. the mean would slowly approach the new data), because the confidence that a change in state has occurred is very low.

As the new data approaches the mean value, there is a low probability that the received data represents an actual change in state of the density. As previously noted, this probability increases as an increasing number of standard deviations away from the mean is received.

In the operation of the present invention, the detected counts are processed by the comparator 17 and output to the count register 25 and subsequently to the computer 26 on a periodic basis. Ten of these counts are accumulated, and the average frequency of the total is compared to a previously obtained mean. The number of standard deviations the accumulated count is from the mean is used together with a dampening factor (entered by the user of the present invention, or from the filter subprogram of the present invention) to develop a weighting factor, which reflects the sensitivity of the filter system of the present invention. The weighting factor is used to determine a new mean, and this mean is used to display a new density.

The digital filter of the present invention is described herein with respect to a radioactive densometer, however, it should be noted that the filter is applicable to any system wherein data is randomly varied about a mean and where the standard deviation is equal to the square root of the mean, such as in many types of well logging.

The present invention greatly reduces response time to an actual change in state of the density by filtering out the random data from the data which indicates that an actual change has occurred and that therefore the weighting factor must be increased to quickly reflect a change in state, such as fluid density.

The weighting factor is determined by taking the mean, or the average frequency ($f_{o(n)}$) of previously examined samples of counts. The frequency ($f_{(n+1)}$), which is the average frequency of the next successive one second sample of accumulated counts, is then subtracted from the initial average frequency and the absolute value of the difference is taken. Next, the standard deviation ($\sigma$) is determined by taking the square root of the initial average frequency.

$$\sigma = \sqrt{f_{o(n)}}$$

The standard deviation ($\sigma$) is then multiplied by a dampening factor (d), a constant the value of which is dependent upon the parameters and operating characteristics of the system, such as whether a cementing, or stimulation type job is being undertaken, and the type and size of radioactive densometer utilized. It has been determined through research, development, field testing and engineering that a value of d=8 works exceedingly well with the filter of the present invention, but any positive number may be used. Finally, the weighting factor is calculated by dividing the absolute value of the difference between the initial average frequency ($f_{o(n)}$), or mean and next successive average frequency ($f_{(n+1)}$) by the product of the standard deviation and the dampening factor. Hence, the following equation describes the above stated relationship.

$$W = \frac{|f_{o(n)} - f_{(n+1)}|}{\sigma d}$$

A new frequency value, which translates into a new density value, is calculated by using a portion of the initial average frequency plus a portion of the next successive average frequency. The portion of the initial average frequency used is one minus the weighting factor. The portion of the next successive average frequency used is the weighting factor. This relationship is described by the following equation:

$$f_{o(n+1)} = f_{o(n)}(1-W) + f_{(n+1)}W$$

For example, let
$f_o = 10,000$
$f_1 = 10,000$
$d = 8$
Then, $$W = \frac{|f_0 - f_1|}{\sigma 8}$$

where, $$\sigma = \sqrt{f_0} = \sqrt{10,000} = 100$$

Hence, $$W = \frac{100}{8(100)} = \frac{1}{8} = 12.5\%$$

Therefore, $$\begin{aligned} f_{o(n+1)} &= 10,000 \left[1 - \frac{1}{8}\right] + 10,100 \left[\frac{1}{8}\right] \\ &= 10,000 \left[\frac{7}{8}\right] + 10,100 \left[\frac{1}{8}\right] \\ &= 8750 \text{ counts} + 1262.5 \text{ counts} \\ &= 10,012.5 \text{ counts} \end{aligned}$$

It can be seen from the above discussion and FIG. 3 that as the weighting factor approaches zero, $f_{o(n+1)}$ approaches $f_{o(n)}$. Conversely, as the weighting factor approaches one, $f_{o(n+1)}$ approaches $f_{(n+1)}$. Thus, as the weighting factor approaches zero, there is a smaller probability that an actual change in state has occurred and a greater probability that any fluctuation in the counts is due to a random variation. However, as the weighting factor approaches one, there is a greater probability that a change in state has in fact occurred and a smaller probability that the fluctuation in frequency was due to a random variation.

It is known from probability that the greater number of standard deviations a value is from the mean (in the present case, $f_{o(n)}$), the greater likelihood that an actual change has occurred. FIG. 3 illustrates the poisson distribution of a random variable, shown as a "bell" shaped curve. Since $f_{o(n)}$ is much greater than 1, this poisson curve approximates the normal curve. Additionally, a linear approximation is depicted which extends from the vertex of the bell curve outwardly in each direction and intersects the horizontal axis at points +d and −d on either side of the line $f_{o(n)}$, which is also zero standard deviations. The value chosen for d will affect the speed with which the filter of the present invention operates.

Figure 2:
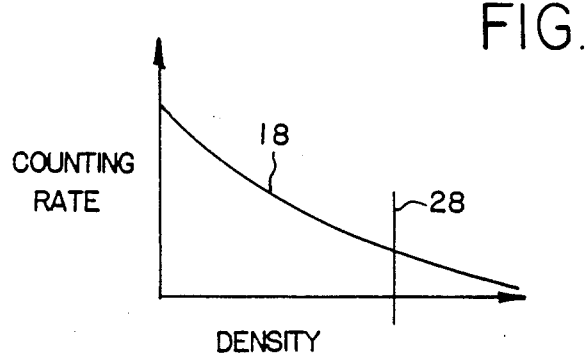
FIG. 2 is a graph illustrating density with respect to mean count rate.

Once it is determined that an actual change in the state (density) has occurred, i.e. $f_{o(n+1)}$ has been calculated, then the density output is updated and displayed on recorder 27 by using the following conversion equation.

$$\rho = K_1 \ln\left(\frac{f_{o(n)}}{K_2}\right)$$

where
$\rho$ = density
$K_2$ = frequency when the bore 12 is empty
$\ln$ = natural logarithm
$K_1$ = constant
$f_{o(n)}$ = mean frequency It should be noted that a plot of the counting rate versus density is illustrated by the curve 18 in FIG. 2.

As stated above, the filter of the present invention uses a linear approximation (see FIG. 3) to determine if an actual change in state has occurred. It should be noted that poisson's distribution, or the normal distribution, or "bell" curve could be utilized to make this determination. However, the present invention is directed towards an embodiment wherein the microprocessor 26 does not have the capacity to determine the distribution of counts along the bell shaped curve within the time limit required by the present invention. The present invention is able to reliably determine when an actual change in state occurs using a linear approximation, without requiring existing microprocessors, already in the field, to be upgraded. Further, use of the filter system of the present invention improves the response time for large changes in density from five (5) to two (2) seconds, and improves response time for small changes in density from twenty (20) to six (6) seconds.

Figure 4A:
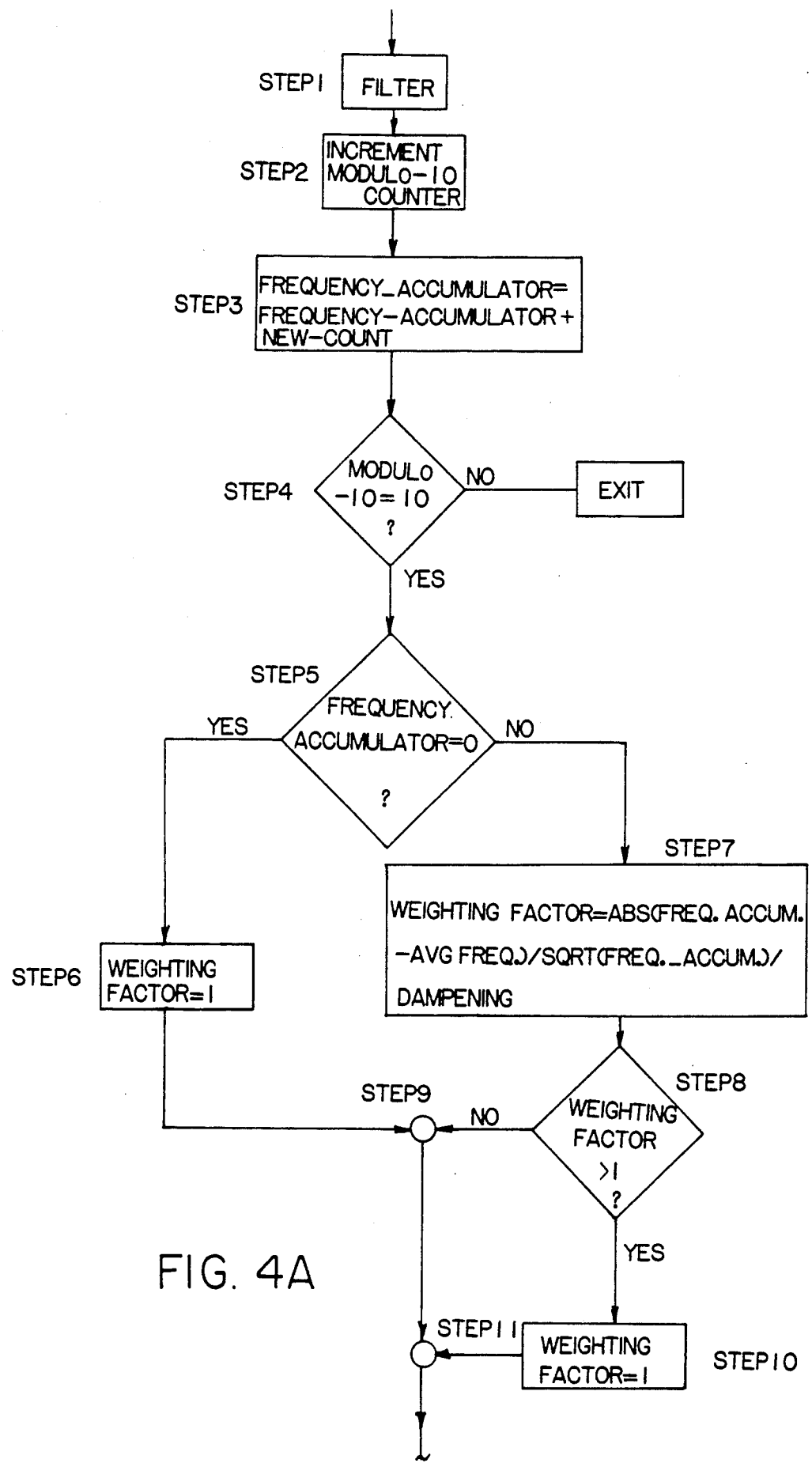
FIGS. 4A and 4B are flow charts for use with a microprocessor, to process the data for obtaining fast response times and indications to changes in state of signals which vary randomly about a mean.
Figure 4B:
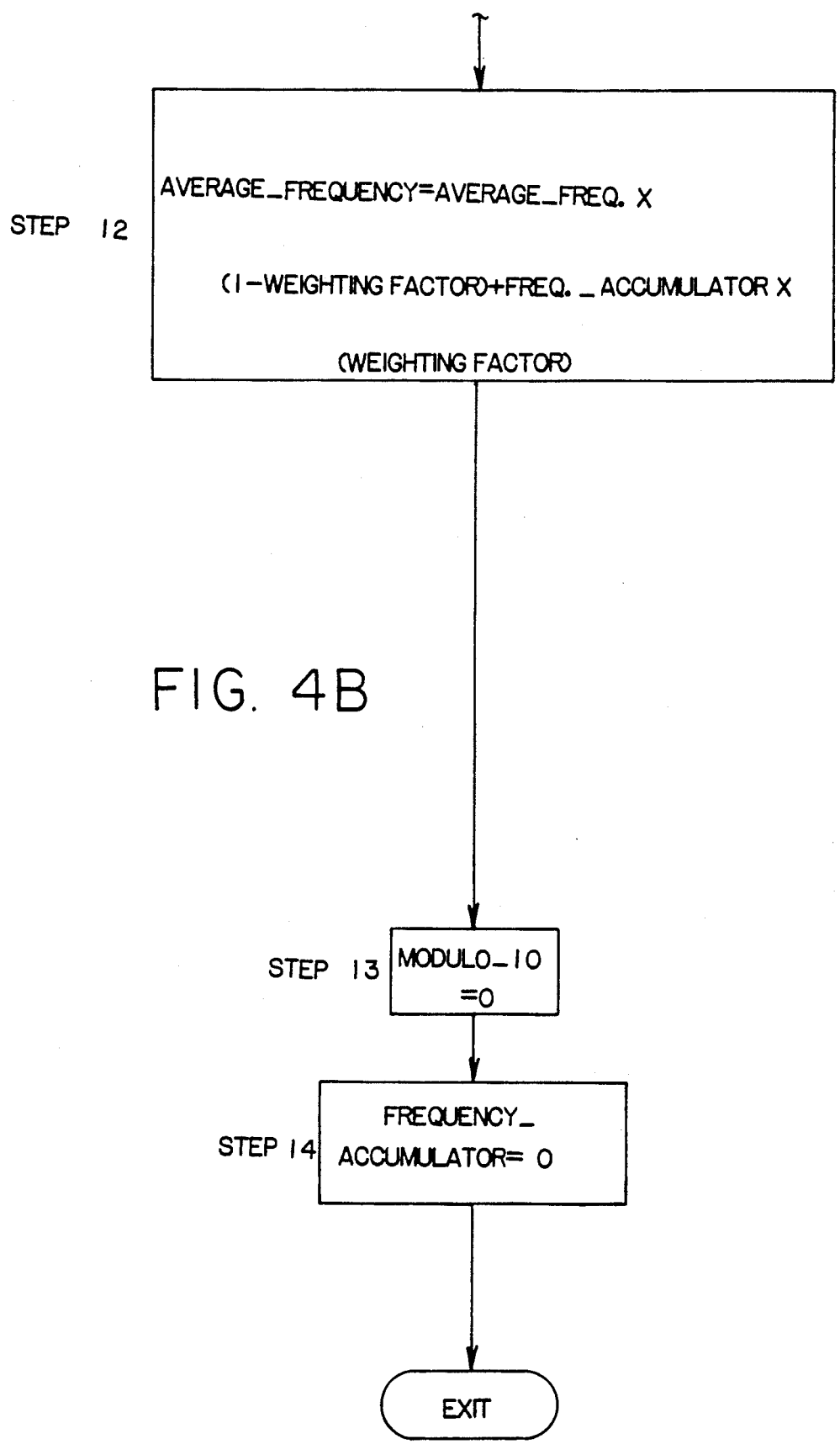

The filter subprogram of the present invention input to CPU 26 will now be described in detail with regard to FIGS. 4A and 4B.

At step 1, the filter subprogram of the present invention is accessed. No processing is performed in step 1. It represents only a location where other subprograms can access the filter subprogram. This subprogram is normally accessed once each time the 10 hertz clock 49 sends a signal. Step 2 increments the modulo 10 counter so that the subprogram can determine when ten, 0.1 second intervals have occurred. Next, in step 3 an accumulator adds any counts stored therein with any new counts from the count register 25.

Step 4 checks that ten counts have been accumulated, i.e. that the clock 49 has signaled ten times. If ten counts have not been received then the filter subprogram is exited. But, if there are ten accumulated counts, then the system proceeds to step 5, where it is determined whether the accumulator is equal to zero, i.e. if zero counts are currently stored therein. If the accumulator is equal to zero then the system proceeds to step 6 where the weighting factor, is set equal to one. Flow of control in the subprogram then proceeds to step 9.

If, at step 5, the accumulator is not equal to zero, then step 7 determines the weighting factor and the system continues to the next step. Step 8 determines if the weighting factor is greater than one. If not, then flow of control in the subprogram continues at step 9. Should the weighting factor be greater than one, then step 10 sets the value equal to one, thus limiting the weighting factor to one hundred percent. Step 11 and step 9 are collection nodes. That is, they show where flows of control combine. No processing occurs at collection nodes.

Next, the filter subprogram proceeds to step 12 where a new average frequency, or mean, is determined by multiplying the initial average frequency by, one minus the weighting factor, and adding this product to the product of the average frequency of counts in the accumulator and the weighting factor.

Step 13 resets the modulo 10 counter to zero, i.e. a new sample period begins, and step 14 resets the average frequency of counts in the accumulator to zero such that the average frequency for the next successive sample of counts can be determined. The filter subprogram then exits and no further filter processing is made until 0.1 seconds later when processing begins again at step 1.

While this system is particularly adapted to the measurement of a cement or proppant slurry where good resolution of density measurement is required along with good accuracy, fast response, and high stability, other adaptations and advantages of the invention will be readily apparent to one skilled in the art to which the invention pertains from a reading of the foregoing. It is accordingly intended that the foregoing description be illustrative only and that the scope of the invention be limited only by the language, with a full range of equivalents, of the appended claims.

What is claimed is:

1. An apparatus utilized by a radiation detection system, comprising:
   tubular means for conveying a fluid therethrough;
   a radioactive source means, disposed adjacent said tubular means, for emitting radiation having random intensity over a relatively short period of time and a constant intensity over a relatively long period of time;
   detection means, disposed diametrically opposite said radiation source means and adjacent said tubular means, for detecting said radiation, and for converting said radiation into electrical signals, said radiation being absorbed by said fluid based upon a density thereof and the radiation detected being a function of the fluid density;
   timing means for sampling said electrical signals for a specific time period; and
   computer means for processing said sampled electrical signals by filtering said electrical signals and by adjusting the present detected density value relative to the previous density value, said computer means utilizing a weighting factor based upon the absolute value of a difference between an average frequency of an initial group of sampled electrical signals, said difference being divided by the product of a standard deviation of said initial average frequency and a dampening factor capable of varying the speed by which said computer means processes said sampled electrical signals.

2. A system according to claim 1 wherein said dampening factor is an arbitrarily determined positive number.

3. A system according to claim 1, wherein said dampening factor may be stored in, or manually input to said computer means.

4. A method for use by a radiation detection system, comprising the steps of:
   providing a radioactive source which emits radiation having random intensity over a relatively short time period and constant intensity over a relatively long time period;
   providing a detector, linearly aligned with said radioactive source, for detecting said radiation;
   flowing a fluid of a certain density between said detector and said radioactive source;
   detecting said radiation, the amount of said radiation detected being a function of the density of said fluid;
   converting said radiation into electrical signals;
   sampling said electrical signals over a certain period of time; and
   processing said sampled electrical signals to filter said electrical signals by:
      determining a first percentage of an average frequency of occurrence of electrical signals sampled during an initial sample period;
      determining a second percentage of an average frequency of occurrence of electrical signals sampled during a next successive sample period;
      adding a first percentage to said second percentage; and
      wherein the steps of determining a first and second percentage include determining a weighting factor and using the same weighting factor in determining each of said first and second percentages.

5. A method according to claim 4 wherein said step of determining said weighting factor comprises the steps of:
   determining said average frequency of occurrence of said electrical signals sampled during the initial sample period;
   determining said average frequency of occurrence of said electrical signals sampled during the next successive sample period; calculating a standard deviation of said initially sampled electrical signals by taking the square root of said initial average frequency;
   selecting a dampening factor which affects the speed with which said sampled electrical signals can be processed;
   subtracting said determined next successive average frequency for the next successive sample period from said initial average frequency and taking the absolute value thereof; and
   dividing the product of said standard deviation and said dampening factor into said absolute value.

6. A method according to claim 5 wherein said step of determining said first percentage includes the step of multiplying said initial average frequency by the difference between said weighting factor and one.

7. A method according to claim 6 wherein said step of determining said second percentage comprises the step of multiplying said next successive average frequency by said weighting factor.

8. A method according to claim 7 wherein said second percentage is in a range of zero to one hundred percent.

9. A method according to claim 6 wherein said first percentage is at least zero.

10. A method according to claim 9 wherein said step of processing further comprises the steps of:
   setting said initial average frequency equal to said next successive average frequency; and sampling a next successive group of electrical signals and determining the average frequency of occurrence thereof.

11. A method according to claim 9 wherein the method for use by a radiation detection system further comprises the steps of:
translating the added said first percentage and said second percentage into a value representing the density of said fluid; and
displaying said density value.

12. An apparatus for monitoring the density of a fluid, comprising:
detection means for detecting from a fluid randomly generated signals responsive to density of the fluid and for developing electrical signals in response to the detected randomly generated signals;
sampling means for sampling groups of said electrical signals over specific intervals of time, said sampling means including a counter connected to said detection means so that said counter generates a count of the number of said electrical signals developed during a respective predetermined interval of time, said count thereby defining the frequency of said electrical signals during the respective interval of time and said count representative of the density of the fluid during the respective interval of time; and
computer means for filtering said counts for determining whether an actual change in the density of the fluid has occurred, said computer means includes means for calculating a weighting factor in response to a standard deviation and a selected dampening factor and for calculating with said weighting factor a first percentage of an average frequency of an initial predetermined number of said counts and a second percentage of an average frequency of a next predetermined number of said counts, said computer means further including means for adding said first percentage to said second percentage for defining a new average frequency for a next initial predetermined number of said counts, wherein said new average frequency is a measurement of the density of the fluid so that a change in the density is indicated when said new average frequency is different from said average frequency of the respective initial predetermined number of said counts.

13. A system for measuring density, comprising:
means for generating signals in response to a density to be measured and a source of radioactivity randomly varying about a mean during predetermined periods of time;
means for sampling said signals over said predetermined periods of time, said sampling means including a counter connected to said generating means so that said counter provides as a respective sample a count of the number of said signals generated during a respective predetermined period of time, said count thereby defining the frequency of said signals during the respective period of time and said count representative of the density during the respective period of time; and
means, connected to said counter, for processing said sampled signals to measure the density by filtering said samples of signals by adjusting the presently sampled signals relative to a previous sample of said signals utilizing a weighting factor which is used to determine a percentage of an average frequency of occurrence $f_{0(n)}$, of said signals sampled over a previous predetermined time period, and said weighting factor also being used to determine a percentage of an average frequency of occurrence $f_{(n+1)}$, of said presently sampled signals, wherein said weighting factor equals $$\frac{|f_{0(n)} - f_{(n+1)}|}{\sigma d},$$

where $\sigma = \sqrt{f_{0(n)}}$ and d=a selected dampening factor, said means for processing including means for adding said percentage of $f_{0(n)}$ and said percentage of $f_{(n+1)}$ to define a sum $f_{0(n+1)}$ as a measure of the (parameter) density.

* * * * *

UNITED STATES PATENT AND TRADEMARK OFFICE
CERTIFICATE OF CORRECTION

PATENT NO. : 5,023,819
DATED : June 11, 1991
INVENTOR(S) : Alan J. Pitts

It is certified that error appears in the above-indentified patent and that said Letters Patent is hereby corrected as shown below:

In column 10, line 41, delete the word [parameter].

Signed and Sealed this

Second Day of August, 1994

Attest:

BRUCE LEHMAN

*Attesting Officer*  *Commissioner of Patents and Trademarks*